(12) United States Patent
Wei

(10) Patent No.: US 7,713,748 B2
(45) Date of Patent: May 11, 2010

(54) METHOD OF REDUCING THE SENSITIVITY OF ASSAY DEVICES

(75) Inventor: Ning Wei, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 846 days.

(21) Appl. No.: 10/718,996

(22) Filed: Nov. 21, 2003

(65) Prior Publication Data

US 2010/0081146 A1    Apr. 1, 2010

(51) Int. Cl.
*G01N 21/00* (2006.01)
*G01N 15/06* (2006.01)
*G01N 21/76* (2006.01)
*G01N 33/53* (2006.01)
*G01N 33/543* (2006.01)
*G01N 33/544* (2006.01)
*G01N 21/77* (2006.01)
*G01N 33/566* (2006.01)
*G01N 31/22* (2006.01)
*C12M 1/34* (2006.01)
*C12M 3/00* (2006.01)
*C12Q 1/00* (2006.01)

(52) U.S. Cl. .......................... 436/518; 435/4; 435/7.1; 435/287.1; 435/287.2; 435/287.7; 435/287.8; 435/288.7; 422/55; 422/56; 422/61; 422/68.1; 422/82.05; 436/164; 436/169; 436/501; 436/528; 436/172; 436/807

(58) Field of Classification Search ................ 422/55, 422/56, 61, 68.1, 82.05; 435/4, 7.1, 287.1, 435/287.2, 287.7, 287.8, 288.7; 436/501, 436/518, 528, 164, 169, 172, 807
See application file for complete search history.

(56) References Cited

U.S. PATENT DOCUMENTS

| 1,366,241 | A | 1/1921 | Burch |
| 3,700,623 | A | 10/1972 | Keim |
| 3,772,076 | A | 11/1973 | Keim |
| 4,094,647 | A | 6/1978 | Deutsch et al. |
| 4,110,529 | A | 8/1978 | Stoy |
| 4,115,535 | A | 9/1978 | Giaever |

(Continued)

FOREIGN PATENT DOCUMENTS

EP    0073593 A1    3/1983

(Continued)

OTHER PUBLICATIONS

Abstract of Japanese Patent No. JP 8062214, Mar. 8, 1996.
Abstract of Article—*Factors influencing the formation of hollow ceramic microspheres by water extraction of colloidal droplets*, J. Mater. Res., vol. 10, No. 1, p. 84.

(Continued)

*Primary Examiner*—Gailene R Gabel
*Assistant Examiner*—Jacqueline Diramio
(74) *Attorney, Agent, or Firm*—Dority & Manning, P.A.

(57) ABSTRACT

A flow-through assay device for detecting the presence or quantity of an analyte residing in a test sample is provided. The device utilizes a scavenging zone that contains a capture reagent for the analyte of interest. The capture reagent may capture a quantity of the analyte that is less than or equal to a predefined base quantity of the analyte, such as a quantity considered "normal" for a particular test sample. Thus, the capture reagent is able to prevent some of the analyte from being detected. In this manner, the sensitivity of the assay device may be reduced in a simple, inexpensive, yet effective manner.

18 Claims, 4 Drawing Sheets

U.S. PATENT DOCUMENTS

| | | |
|---|---|---|
| 4,168,146 A | 9/1979 | Grubb et al. |
| RE30,267 E | 5/1980 | Bruschi |
| 4,210,723 A | 7/1980 | Dorman et al. |
| 4,235,601 A | 11/1980 | Deutsch et al. |
| 4,275,149 A | 6/1981 | Litman et al. |
| 4,312,228 A | 1/1982 | Wohltjen |
| 4,363,874 A | 12/1982 | Greenquist |
| 4,366,241 A | 12/1982 | Tom et al. |
| 4,374,925 A | 2/1983 | Litman et al. |
| 4,385,126 A | 5/1983 | Chen et al. |
| 4,426,451 A | 1/1984 | Columbus |
| 4,427,836 A | 1/1984 | Kowalski et al. |
| 4,435,504 A | 3/1984 | Zuk et al. |
| 4,441,373 A | 4/1984 | White |
| 4,442,204 A | 4/1984 | Greenquist et al. |
| 4,444,592 A | 4/1984 | Ludwig |
| 4,477,635 A | 10/1984 | Mitra |
| 4,480,042 A | 10/1984 | Craig et al. |
| 4,533,499 A | 8/1985 | Clark et al. |
| 4,533,629 A | 8/1985 | Litman et al. |
| 4,534,356 A | 8/1985 | Papadakis |
| 4,537,657 A | 8/1985 | Keim |
| 4,537,861 A | 8/1985 | Elings et al. |
| 4,540,659 A | 9/1985 | Litman et al. |
| 4,552,458 A | 11/1985 | Lowne |
| 4,561,286 A | 12/1985 | Sekler et al. |
| 4,562,157 A | 12/1985 | Lowe et al. |
| 4,586,695 A | 5/1986 | Miller |
| 4,595,661 A | 6/1986 | Cragle et al. |
| 4,596,697 A | 6/1986 | Ballato |
| 4,614,723 A | 9/1986 | Schmidt et al. |
| 4,632,559 A | 12/1986 | Brunsting |
| 4,661,235 A | 4/1987 | Krull et al. |
| 4,698,262 A | 10/1987 | Schwartz et al. |
| 4,703,017 A | 10/1987 | Campbell et al. |
| 4,722,889 A | 2/1988 | Lee et al. |
| 4,727,019 A | 2/1988 | Valkirs et al. |
| 4,731,337 A | 3/1988 | Luotola et al. |
| 4,742,011 A | 5/1988 | Blake et al. |
| 4,743,542 A | 5/1988 | Graham, Jr. et al. |
| 4,743,560 A | 5/1988 | Campbell et al. |
| 4,776,944 A | 10/1988 | Janata et al. |
| 4,806,312 A | 2/1989 | Greenquist |
| 4,835,099 A | 5/1989 | Mize et al. |
| 4,837,168 A | 6/1989 | de Jaeger et al. |
| 4,842,783 A | 6/1989 | Blaylock |
| 4,843,000 A | 6/1989 | Litman et al. |
| 4,843,021 A | 6/1989 | Noguchi et al. |
| 4,844,613 A | 7/1989 | Batchelder et al. |
| 4,849,338 A | 7/1989 | Litman et al. |
| 4,855,240 A | 8/1989 | Rosenstein et al. |
| 4,857,453 A | 8/1989 | Ullman et al. |
| 4,867,908 A | 9/1989 | Recktenwald et al. |
| 4,877,586 A | 10/1989 | Devaney, Jr. et al. |
| 4,877,747 A | 10/1989 | Stewart |
| 4,889,816 A | 12/1989 | Davis et al. |
| 4,895,017 A | 1/1990 | Pyke et al. |
| 4,904,583 A | 2/1990 | Mapes et al. |
| 4,916,056 A | 4/1990 | Brown, III et al. |
| 4,917,503 A | 4/1990 | Bhattacharjee |
| 4,920,045 A | 4/1990 | McFarland et al. |
| 4,940,734 A | 7/1990 | Ley et al. |
| 4,954,435 A | 9/1990 | Krauth |
| 4,956,302 A | 9/1990 | Gordon et al. |
| 4,963,498 A | 10/1990 | Hillman et al. |
| 4,973,670 A | 11/1990 | McDonald et al. |
| 4,978,625 A | 12/1990 | Wagner et al. |
| 4,980,298 A | 12/1990 | Blake et al. |
| 4,992,385 A | 2/1991 | Godfrey |
| 5,003,178 A | 3/1991 | Livesay |
| 5,023,053 A | 6/1991 | Finlan |
| 5,026,653 A | 6/1991 | Lee et al. |
| 5,035,863 A | 7/1991 | Finlan et al. |
| 5,055,265 A | 10/1991 | Finlan |
| 5,063,081 A | 11/1991 | Cozzette et al. |
| 5,064,619 A | 11/1991 | Finlan |
| 5,073,340 A | 12/1991 | Covington et al. |
| 5,075,077 A | 12/1991 | Durley, III et al. |
| 5,075,078 A | 12/1991 | Osikowicz et al. |
| 5,076,094 A | 12/1991 | Frye et al. |
| 5,096,671 A | 3/1992 | Kane et al. |
| 5,114,676 A | 5/1992 | Leiner et al. |
| 5,120,643 A | 6/1992 | Ching et al. |
| 5,120,662 A | 6/1992 | Chan et al. |
| 5,124,254 A | 6/1992 | Hewlins et al. |
| 5,134,057 A | 7/1992 | Kuypers et al. |
| 5,137,609 A | 8/1992 | Manian et al. |
| 5,143,854 A | 9/1992 | Pirrung et al. |
| 5,145,784 A | 9/1992 | Cox et al. |
| 5,149,622 A | 9/1992 | Brown et al. |
| 5,152,758 A | 10/1992 | Kaetsu et al. |
| 5,156,953 A | 10/1992 | Litman et al. |
| 5,166,079 A | 11/1992 | Blackwood et al. |
| 5,179,288 A | 1/1993 | Miffitt et al. |
| 5,182,135 A | 1/1993 | Giesecke et al. |
| 5,183,740 A | 2/1993 | Ligler et al. |
| 5,185,127 A | 2/1993 | Vonk |
| 5,196,350 A | 3/1993 | Backman et al. |
| 5,200,084 A | 4/1993 | Liberti et al. |
| 5,208,143 A | 5/1993 | Henderson et al. |
| 5,208,535 A | 5/1993 | Nakayama et al. |
| 5,221,454 A | 6/1993 | Manian et al. |
| 5,225,935 A | 7/1993 | Watanabe et al. |
| 5,234,813 A | 8/1993 | McGeehan et al. |
| 5,235,238 A | 8/1993 | Nomura et al. |
| 5,238,815 A | 8/1993 | Higo et al. |
| 5,242,828 A | 9/1993 | Bergström et al. |
| 5,252,459 A | 10/1993 | Tarcha et al. |
| 5,262,299 A | 11/1993 | Evangelista et al. |
| 5,268,306 A | 12/1993 | Berger et al. |
| 5,275,785 A | 1/1994 | May et al. |
| 5,304,468 A | 4/1994 | Phillips et al. |
| 5,314,923 A | 5/1994 | Cooke et al. |
| 5,316,727 A | 5/1994 | Suzuki et al. |
| 5,320,944 A | 6/1994 | Okada et al. |
| 5,321,492 A | 6/1994 | Detwiler et al. |
| 5,327,225 A | 7/1994 | Bender et al. |
| 5,330,898 A | 7/1994 | Bar-Or et al. |
| 5,342,759 A | 8/1994 | Litman et al. |
| 5,352,582 A | 10/1994 | Lichtenwalter et al. |
| 5,356,782 A | 10/1994 | Moorman et al. |
| 5,358,852 A | 10/1994 | Wu |
| 5,369,717 A | 11/1994 | Attridge |
| 5,374,531 A | 12/1994 | Jensen |
| 5,374,563 A | 12/1994 | Maule |
| 5,376,255 A | 12/1994 | Gumbrecht et al. |
| 5,387,503 A | 2/1995 | Selmer et al. |
| 5,395,754 A | 3/1995 | Lambotte et al. |
| 5,415,842 A | 5/1995 | Maule |
| 5,418,136 A | 5/1995 | Miller et al. |
| 5,424,219 A | 6/1995 | Jirikowski |
| 5,428,690 A | 6/1995 | Bacus et al. |
| 5,432,057 A | 7/1995 | Litman et al. |
| 5,436,161 A | 7/1995 | Bergström et al. |
| 5,445,971 A | 8/1995 | Rohr |
| 5,451,683 A | 9/1995 | Barrett et al. |
| 5,455,475 A | 10/1995 | Josse et al. |
| 5,464,741 A | 11/1995 | Hendrix |
| 5,466,574 A | 11/1995 | Liberti et al. |
| 5,467,778 A | 11/1995 | Catt et al. |
| 5,468,606 A | 11/1995 | Bogart et al. |
| 5,482,830 A | 1/1996 | Bogart et al. |
| 5,482,867 A | 1/1996 | Barrett et al. |
| 5,484,867 A | 1/1996 | Lichtenhan et al. |

| Patent | Date | Inventor |
|---|---|---|
| 5,489,678 A | 2/1996 | Fodor et al. |
| 5,489,988 A | 2/1996 | Ackley et al. |
| 5,492,840 A | 2/1996 | Malmqvist et al. |
| 5,500,350 A | 3/1996 | Baker et al. |
| 5,504,013 A | 4/1996 | Senior |
| 5,508,171 A | 4/1996 | Walling et al. |
| 5,510,481 A | 4/1996 | Bednarski et al. |
| 5,512,131 A | 4/1996 | Kumar et al. |
| 5,514,559 A | 5/1996 | Markert-Hahn et al. |
| 5,514,785 A | 5/1996 | Van Ness et al. |
| 5,516,635 A | 5/1996 | Ekins et al. |
| 5,518,689 A | 5/1996 | Dosmann et al. |
| 5,518,883 A | 5/1996 | Soini |
| 5,521,102 A | 5/1996 | Boehringer et al. |
| 5,527,711 A | 6/1996 | Tom-Moy et al. |
| 5,534,132 A | 7/1996 | Vreeke et al. |
| 5,554,539 A | 9/1996 | Chadney et al. |
| 5,554,541 A | 9/1996 | Malmqvist et al. |
| 5,569,608 A | 10/1996 | Sommer |
| 5,571,684 A | 11/1996 | Lawrence et al. |
| 5,573,909 A | 11/1996 | Singer et al. |
| 5,573,919 A | 11/1996 | Kearns et al. |
| 5,585,279 A | 12/1996 | Davidson |
| 5,589,401 A | 12/1996 | Hansen et al. |
| 5,591,581 A | 1/1997 | Massey et al. |
| 5,591,645 A | 1/1997 | Rosenstein |
| 5,596,414 A | 1/1997 | Tyler |
| 5,599,668 A | 2/1997 | Stimpson et al. |
| 5,602,040 A | 2/1997 | May et al. |
| 5,610,077 A | 3/1997 | Davis et al. |
| 5,618,732 A | 4/1997 | Pease et al. |
| 5,618,888 A | 4/1997 | Choi et al. |
| 5,620,850 A | 4/1997 | Bamdad et al. |
| 5,622,871 A | 4/1997 | May et al. |
| 5,637,509 A | 6/1997 | Hemmilä et al. |
| 5,647,994 A | 7/1997 | Tuunanen et al. |
| 5,656,503 A | 8/1997 | May et al. |
| 5,658,443 A | 8/1997 | Yamamoto et al. |
| 5,663,213 A | 9/1997 | Jones et al. |
| 5,670,381 A | 9/1997 | Jou et al. |
| 5,672,256 A | 9/1997 | Yee |
| 5,700,636 A | 12/1997 | Sheiness et al. |
| 5,714,389 A | 2/1998 | Charlton et al. |
| 5,726,064 A | 3/1998 | Robinson et al. |
| 5,731,147 A | 3/1998 | Bard et al. |
| 5,736,188 A | 4/1998 | Alcock et al. |
| 5,753,517 A | 5/1998 | Brooks et al. |
| 5,770,416 A | 6/1998 | Lihme et al. |
| 5,780,308 A | 7/1998 | Ching et al. |
| 5,788,863 A | 8/1998 | Milunic |
| 5,795,470 A | 8/1998 | Wang et al. |
| 5,795,543 A | 8/1998 | Poto et al. |
| 5,798,273 A | 8/1998 | Shuler et al. |
| 5,811,526 A | 9/1998 | Davidson |
| 5,827,748 A | 10/1998 | Golden |
| 5,834,226 A | 11/1998 | Maupin |
| 5,837,429 A | 11/1998 | Nohr et al. |
| 5,837,546 A | 11/1998 | Allen et al. |
| 5,837,547 A | 11/1998 | Schwartz |
| 5,843,692 A | 12/1998 | Phillips et al. |
| 5,852,229 A | 12/1998 | Josse et al. |
| 5,876,944 A | 3/1999 | Kuo |
| 5,885,527 A | 3/1999 | Buechler |
| 5,906,921 A | 5/1999 | Ikeda et al. |
| 5,910,286 A | 6/1999 | Lipskier |
| 5,910,447 A | 6/1999 | Lawrence et al. |
| 5,910,940 A | 6/1999 | Guerra |
| 5,922,537 A | 7/1999 | Ewart et al. |
| 5,922,550 A | 7/1999 | Everhart et al. |
| 5,945,281 A | 8/1999 | Prabhu |
| 5,951,492 A | 9/1999 | Douglas et al. |
| 5,962,995 A | 10/1999 | Avnery |
| 5,968,839 A | 10/1999 | Blatt et al. |
| 5,989,924 A | 11/1999 | Root et al. |
| 5,989,926 A | 11/1999 | Badley et al. |
| 5,993,805 A | 11/1999 | Sutton et al. |
| 5,998,221 A | 12/1999 | Malick et al. |
| 6,004,530 A | 12/1999 | Sagner et al. |
| 6,020,047 A | 2/2000 | Everhart |
| 6,027,904 A | 2/2000 | Devine et al. |
| 6,027,944 A | 2/2000 | Robinson et al. |
| 6,030,792 A | 2/2000 | Otterness et al. |
| 6,030,840 A | 2/2000 | Mullinax et al. |
| 6,033,574 A | 3/2000 | Siddiqi |
| 6,048,623 A | 4/2000 | Everhart et al. |
| 6,057,165 A | 5/2000 | Mansour |
| 6,060,256 A | 5/2000 | Everhart et al. |
| 6,077,669 A | 6/2000 | Little et al. |
| 6,080,391 A | 6/2000 | Tsuchiya et al. |
| 6,084,683 A | 7/2000 | Bruno et al. |
| 6,087,184 A | 7/2000 | Magginetti et al. |
| 6,099,484 A | 8/2000 | Douglas et al. |
| 6,103,537 A | 8/2000 | Ullman et al. |
| 6,117,090 A | 9/2000 | Caillouette |
| 6,130,100 A | 10/2000 | Jobling et al. |
| 6,133,048 A | 10/2000 | Penfold et al. |
| 6,136,549 A | 10/2000 | Feistel |
| 6,136,611 A | 10/2000 | Saaski et al. |
| 6,139,961 A | 10/2000 | Blankenship et al. |
| 6,151,110 A | 11/2000 | Markart |
| 6,156,271 A | 12/2000 | May |
| 6,165,798 A | 12/2000 | Brooks |
| 6,171,780 B1 | 1/2001 | Pham et al. |
| 6,171,870 B1 | 1/2001 | Freitag |
| 6,174,646 B1 | 1/2001 | Hirai et al. |
| 6,177,281 B1 | 1/2001 | Manita |
| 6,180,288 B1 | 1/2001 | Everhart et al. |
| 6,183,972 B1 | 2/2001 | Kuo et al. |
| 6,184,042 B1 | 2/2001 | Neumann et al. |
| 6,187,269 B1 | 2/2001 | Lancesseru et al. |
| 6,194,220 B1 | 2/2001 | Malick et al. |
| 6,200,820 B1 | 3/2001 | Hansen et al. |
| 6,221,238 B1 | 4/2001 | Grundig et al. |
| 6,221,579 B1 | 4/2001 | Everhart et al. |
| 6,234,974 B1 | 5/2001 | Catt et al. |
| 6,235,241 B1 | 5/2001 | Catt et al. |
| 6,235,471 B1 | 5/2001 | Knapp et al. |
| 6,235,491 B1 | 5/2001 | Connolly |
| 6,241,863 B1 | 6/2001 | Monbouquette |
| 6,242,268 B1 | 6/2001 | Wieder et al. |
| 6,255,066 B1 | 7/2001 | Louderback |
| 6,258,548 B1 * | 7/2001 | Buck .................. 435/7.1 |
| 6,261,779 B1 | 7/2001 | Barbera-Guillem et al. |
| 6,268,222 B1 | 7/2001 | Chandler et al. |
| 6,270,637 B1 | 8/2001 | Crismore et al. |
| 6,271,040 B1 | 8/2001 | Buechler |
| 6,274,324 B1 | 8/2001 | Davis et al. |
| 6,281,006 B1 | 8/2001 | Heller et al. |
| 6,284,472 B1 | 9/2001 | Wei et al. |
| 6,287,783 B1 | 9/2001 | Maynard et al. |
| 6,287,871 B1 | 9/2001 | Herron et al. |
| 6,294,391 B1 | 9/2001 | Badley et al. |
| 6,294,392 B1 | 9/2001 | Kuhr et al. |
| 6,306,665 B1 | 10/2001 | Buck et al. |
| D450,854 S | 11/2001 | Lipman et al. |
| 6,331,438 B1 | 12/2001 | Aylott et al. |
| 6,348,186 B1 | 2/2002 | Sutton et al. |
| 6,352,862 B1 | 3/2002 | Davis et al. |
| 6,362,011 B1 | 3/2002 | Massey et al. |
| 6,368,873 B1 | 4/2002 | Chang et al. |
| 6,368,875 B1 | 4/2002 | Geisberg |
| 6,387,707 B1 | 5/2002 | Seul et al. |
| 6,391,558 B1 | 5/2002 | Henkens et al. |
| 6,399,295 B1 | 6/2002 | Kaylor et al. |
| 6,399,397 B1 | 6/2002 | Zarling et al. |
| 6,399,398 B1 | 6/2002 | Cunningham et al. |

| | | | |
|---|---|---|---|
| 6,407,492 B1 | 6/2002 | Avnery et al. | |
| 6,411,439 B2 | 6/2002 | Nishikawa | |
| 6,413,410 B1 | 7/2002 | Hodges et al. | |
| 6,436,651 B1 | 8/2002 | Everhart et al. | |
| 6,436,722 B1 | 8/2002 | Clark et al. | |
| 6,444,423 B1 | 9/2002 | Meade et al. | |
| 6,448,091 B1 | 9/2002 | Massey et al. | |
| 6,451,607 B1 | 9/2002 | Lawrence et al. | |
| 6,455,861 B1 | 9/2002 | Hoyt | |
| 6,461,496 B1 | 10/2002 | Feldman et al. | |
| 6,468,741 B1 | 10/2002 | Massey et al. | |
| 6,472,226 B1 | 10/2002 | Barradine et al. | |
| 6,479,146 B1 | 11/2002 | Caruso et al. | |
| 6,509,085 B1 | 1/2003 | Kennedy | |
| 6,509,196 B1 | 1/2003 | Brooks et al. | |
| 6,511,814 B1 | 1/2003 | Carpenter | |
| 6,524,864 B2 | 2/2003 | Fernandez de Castro | |
| 6,556,299 B1 | 4/2003 | Rushbrooke et al. | |
| 6,566,508 B2 | 5/2003 | Bentsen et al. | |
| 6,573,040 B2 | 6/2003 | Everhart et al. | |
| 6,579,673 B2 | 6/2003 | McGrath et al. | |
| 6,582,930 B1 | 6/2003 | Ponomarev et al. | |
| 6,585,939 B1 | 7/2003 | Dapprich | |
| 6,607,922 B2 | 8/2003 | LaBorde | |
| 6,613,583 B1 | 9/2003 | Richter et al. | |
| 6,617,488 B1 | 9/2003 | Springer et al. | |
| 6,627,459 B1 | 9/2003 | Tung et al. | |
| 6,653,149 B1 | 11/2003 | Tung et al. | |
| 6,669,908 B2 | 12/2003 | Weyker et al. | |
| 6,670,115 B1 | 12/2003 | Zhang | |
| RE38,430 E | 2/2004 | Rosenstein | |
| 6,720,007 B2 | 4/2004 | Walt et al. | |
| 6,787,368 B1 | 9/2004 | Wong et al. | |
| 6,815,218 B1 | 11/2004 | Jacobson et al. | |
| 6,951,631 B1 | 10/2005 | Catt et al. | |
| 7,044,919 B1 | 5/2006 | Catt et al. | |
| 7,052,831 B2 | 5/2006 | Fletcher et al. | |
| 2001/0055776 A1 | 12/2001 | Greenwalt | |
| 2002/0042149 A1 | 4/2002 | Butlin et al. | |
| 2002/0045273 A1 | 4/2002 | Butlin et al. | |
| 2002/0070128 A1 | 6/2002 | Beckmann | |
| 2002/0146754 A1 | 10/2002 | Kitawaki et al. | |
| 2002/0164659 A1 | 11/2002 | Rao et al. | |
| 2003/0017615 A1 | 1/2003 | Sidwell et al. | |
| 2003/0119202 A1 | 6/2003 | Kaylor et al. | |
| 2003/0119204 A1 | 6/2003 | Wei et al. | |
| 2003/0124739 A1 | 7/2003 | Song et al. | |
| 2003/0162236 A1 | 8/2003 | Harris et al. | |
| 2003/0178309 A1 | 9/2003 | Huang et al. | |
| 2004/0014073 A1 | 1/2004 | Trau et al. | |
| 2004/0043502 A1 | 3/2004 | Song et al. | |
| 2004/0043507 A1 | 3/2004 | Song et al. | |
| 2004/0043511 A1 | 3/2004 | Song et al. | |
| 2004/0106190 A1 | 6/2004 | Yang et al. | |
| 2004/0151632 A1 | 8/2004 | Badley et al. | |
| 2006/0029924 A1 | 2/2006 | Brewster et al. | |

FOREIGN PATENT DOCUMENTS

| | | | |
|---|---|---|---|
| EP | 0205698 A1 | 12/1986 | |
| EP | 0420053 A1 | 4/1991 | |
| EP | 0437287 B1 | 7/1991 | |
| EP | 0703454 A1 | 3/1996 | |
| EP | 0462376 B1 | 7/1996 | |
| EP | 0724156 A1 | 7/1996 | |
| EP | 0745843 A2 | 12/1996 | |
| EP | 0745843 A3 | 12/1996 | |
| EP | 0859230 A1 | 8/1998 | |
| EP | 0898169 B1 | 2/1999 | |
| EP | 1221616 A1 | 7/2002 | |
| EP | 1 255111 A1 | 11/2002 | |
| GB | 2273772 A | 6/1994 | |
| WO | WO 8804777 A1 | 6/1988 | |
| WO | WO 9105999 A2 | 5/1991 | |
| WO | WO 9221769 A1 | 12/1992 | |
| WO | WO 9221770 A1 | 12/1992 | |
| WO | WO 9221975 A1 | 12/1992 | |
| WO | WO 9301308 A1 | 1/1993 | |
| WO | WO 9319370 A1 | 9/1993 | |
| WO | WO 9413835 A1 | 6/1994 | |
| WO | WO 9415193 A1 | 7/1994 | |
| WO | WO 9709620 A1 | 3/1997 | |
| WO | WO 9910742 A1 | 3/1999 | |
| WO | WO 9930131 A1 | 6/1999 | |
| WO | WO 9936777 A1 | 7/1999 | |
| WO | WO 9964864 A1 | 12/1999 | |
| WO | WO 0019199 A1 | 4/2000 | |
| WO | WO 0023805 A1 | 4/2000 | |
| WO | WO 0046839 A2 | 8/2000 | |
| WO | WO 0046839 A3 | 8/2000 | |
| WO | WO 0047983 A1 | 8/2000 | |
| WO | WO 0050891 A1 | 8/2000 | |
| WO | WO 0078917 A1 | 12/2000 | |
| WO | WO 0138873 A2 | 5/2001 | |
| WO | WO 0163299 A1 | 8/2001 | |
| WO | WO 0198765 A1 | 12/2001 | |
| WO | WO 0198785 A2 | 12/2001 | |
| WO | WO 0198795 A1 | 12/2001 | |
| WO | WO 03/008971 A2 | 1/2003 | |
| WO | WO 03/008971 A3 | 1/2003 | |
| WO | WO 03005013 A1 | 1/2003 | |
| WO | WO 200//034056 A3 | 4/2004 | |
| WO | WO 2004/034056 A2 | 4/2004 | |
| WO | WO 2004034056 A2 | 4/2004 | |
| WO | WO 2004034056 A3 | 4/2004 | |

OTHER PUBLICATIONS

Article —*A conductometric biosensor for biosecurity*, Zarini Muhammid-Tahir and Evangelyn C. Alocilja, Biosensors and Bioelectronics 18, 2003, pp. 813-819.

Article —*A Disposable Amperometric Sensor Screen Printed on a Nitrocellulose Strip: A Glucose Biosensor Employing Lead Oxide as an InterferenCe-Removing Agent*, Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.

Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.

Article —*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596- 601.

Article —*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp. 4247-4249.

Article —*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.

Article —*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.

Article —*Analysis of electrical equivalent circuit of quartz crystal resonator loaded with viscous conductive liquids*, Journal of Electroanalytical Chemistry, vol. 379, 1994, pp. 21-33.

Article —*Application of rod-like polymers with ionophores as Langmuir-Blodgett membranes for Si-Based ion sensors*, Sensors & Actuators B, vol. 6, 1992, pp. 211-226.

Article— *Attempts to Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.

Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.

Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.

Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.

Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.

Article— *Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.

Article— *Evaluation of a Time-Resolved Fluorescence Microscope Using a Phosphorescent.Pt-Porphine Model System*, E. J. Hennink, R. de Haas, N. P. Verwoerd, and H. J. Tanke, Cytometry, vol. 24, 1996, pp. 312-320.

Article—*Fabrication of Patterned. Electrically Conducting Polypyrrole Using a Self-Assembled Monolayer: A Route to All-Organic Circuits*, Christopher B. Gorman, Hans A. Biebuyck, and George M. Whitesides, American Chemical Society, 2 pages.

Article —*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.

Article —*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.

Article —*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.

Article—Flow-*Based Microimmunoassay*, Analytical Chemistry, vol. 73, No. 24, Mark A. Hayes, Nolan A. Poison, Allison, N. Phayre, and Antonia A. Garcia, Dec. 15, 2001, pp. 5896-5902.

Article —*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.

Article —*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

Article—*Hollow latex particles: synthesis and applications*, Charles J. McDonald and Michael J. Devon, Advances in Colloid and Interface Science, Vo. 99, 2002, pp. 181-213.

Article — *How to Build a Spectrofluorometer*, Spex Fluorolog 3, Horiba Group, pp. 1-14.

Article —*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.

Article —*Immunoaffinity Based Phosphorescent Sensor Platform for the Detection of Bacterial Spores*, Peter F. Scholl, C. Brent Bargeron, Terry E. Phillips, Tonuny Wong, Sala Abubaker, John D. Groopman, Paul T. Strickland, and Richard C. Benson, Proceedings of SPIE, vol. 3913, 2000, pp. 204-214.

Article —*Inert Phosphorescent Nanospheres as Markers for Optical Assays*, Jens M. Kümer, Ingo Klimant, Christian Krause, Harald Preu, Werner Kunz, and Otto S. Wolfbeis, Bioconjugate Chem., vol. 12, No. 6, 2001, pp. 883-889.

Article —*Intelligent Gels*, Yoshihito Osada and Simon B. Ross-Murphy, Scientific American, May 1993, pp. 82-87.

Article —*Latex Immunoassays*, Leigh B. Bangs, Journal of Clinical Immunoassay, vol. 13, No. 3, 1990, pp. 127-131.

Article —*Longwave luminescent porphyrin probes*, Dmitry B. Papkovsky, Gelii P. Ponomarev, and Otto S. Wolfbeis, Spectrochimica Acta Part A 52, 1996, pp. 1629-1638.

Article —*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.

Article —*Microfabrication by Microcontact Printing Of Self-Assembled Monolyaers*, James L. Wilbur, Armit Kumar, Enoch Kim, and George M. Whitesides, Advanced Materials, vol. 6, No. 7/8,1994, pp. 600- 604.

Article—*Modification of monoclonal and polyclonal IgG with palladium (II) coproporphyrin I: stimulatory and inhibitory functional effects induced by two different methods*, Sergey P. Martsev, Valery A. Preygerzon, Yanina I. Mel'nikova, Zinaida I. Kravchulc, Gely V. Ponomarev, Vitaly E. Lunev, and Alexander P. Savitslcy, Journal of Immunological Methods 186, 1996, pp. 293-304.

Article—*Molecular Design Temperature-Responsive Polymers as Intelligent Materials*, Teruo Okano, Advances in Polymer Science, pp. 179-197.

Article—*Molecular Gradients of w-Substituted Alkanethiols on Gold: Preparation and Characterization*, Bo Liedberg and Pentti Tengvall, Langmuir, vol. II, No. 10, 1995, pp. 3821-3827.

Article—*Monofunctional Derivatives of Coproporphyrins for Phosphorescent Labeling of Proteins and Binding Assays*, Tomás C. O'Riordan, Aleksi E. Soini, and Dmitri B. Papkovsky, Analytical Biochemistry, vol. 290, 2001, pp. 366-375.

Article—*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.

Article—*Near Infrared Phosphorescent Metalloporphrins*, Alexander P. Savitsky Anna V. Savitskaja, Eugeny A. Lukjanetz, Svetlana N. Dashkevich, and Elena A. Malcarova, SPIE, vol. 2980, pp. 352-357.

Article—*New Approach To Producing Patterned Biomolecular Assemblies*, Suresh K. Bhatia, James J. Hickman, and Frances S. Ligler, J. Am. Chem. Soc., vol. 114, 1992, pp. 4433-4434.

Article—*On the use of ZX-LiNbO$_3$ acoustic plate mode devices as detectors for dilute electrolytes*, F. Josse, Z. A. Shana, D. T. Haworth, and S. Liew, Sensors and Actuators B, vol. 9, 1992, pp. 92-112.

Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.

Article—*Optical Biosensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.

Article—*Orientation dependence of surface segregation in a dilute Ni-Au alloy*, W. C. Johnson, N. G. Chavka, R. Ku, J. L. Bomback, and P. P. Wynblatt, J. Vac. Sci. Technol. vol. 15, No. 2, Mar./Apr. 1978, pp. 467-469.

Article—*Patterned Condensation Figures as Optical Diffraction Gratings*, Amit Kumar and George M. Whitesides, Science, vol. 263, Jan. 7, 1994, pp. 60-62.

Article—*Patterned Functionalization of Gold and Single Crystal Silicon via Photochemical Reaction of Surface-Confined Derivatives* of $(n^5-C_5H_5)Mn(CO)_3$, Doris Kang and Mark S. Wrighton, Langmuir, vol. 7, No. 10, 1991, pp. 2169-2174.
Article—*Patterned Metal Electrodeposition Using an Alkanethiolate Mask*, T. P. Moffat and H. Yang, J. Electrochem. Soc., vol. 142, No. 11, Nov. 1995, pp. L220- L222.
Article—*Performance Evaluation of the Phosphorescent Porphyrin Label: Solid-Phase Immunoassay of α-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.
Article—*Phosphorescent porphyrin probes in biosensors and sensitive bioassays*, D. B. Papkovsky, T. O'Riordan, and A. Soini, Biochemical Society Transactions, vol. 28, part 2, 2000, pp. 74-77.
Article—*Photopatterning and Selective Elearoless Metallization of Surface-Attached Ligands*, Walter J. Dressick, Charles S. Dulcey, Jacque H. Georger, Jr., and Jeffrey M. Calvert, American Chemical Society, 2 pages.
Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.
Article—*Polymer Based Lanthanide Luminescent Sensors for the Detection of Nerve Agents*, Amanda L. Jenkins, O. Manuel Uy, and George M. Murray, Analytical Communications, vol., 34, Aug. 1997, pp. 221-224.
Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.
Article—*Principle and Applications of Size-Exclusion Chromatography*, Impact Analytical, pp. 1-3.
Article—*Probing of strong and weak electrolytes with acoustic wave fields*, R. Dahint, D. Grunze, F. Josse, and J. C. Andle, Sensors and Actuators B, vol. 9, 1992, pp. 155-162.
Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.
Article—*Quantitative Prediction of Surface Segregation*, M. P. Seah, Journal of Catalysts, vol. 57, 1979, pp. 450-457.
Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.
Article—*Responsive Gels: Volume Transitions I*, M. Ilavský, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 9 pages.
Article—*Room-Temperature Phosphorescent Palladium—Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.
Article—*Self-Assembled Monolayer Films For Nanofabrication*, Elizabeth A. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.
Article—*Sensing liquid properties with thickness-shear mode resonators*, S. J. Martin, G. C. Frye, and K. O. Wessendorf, Sensors and Actuators A, vol. 44, 1994, pp. 209-218.
Article—*Separation-Free Sandwich Enzyme Immunoassays Using Microporous Gold Electrodes and Self-Assembled Monolayer/Immobolized Capture Antibodies*, Chuanming Duan and Mark E. Meyerhoff, Analytical Chemistry, vol. 66, No. 9, May 1, 1994, pp. 1369-1377.
Article—*Solid Substrate Phosphorescent Immunoassay Based On Bioconjugated Nanaparticles*, Gaoquan Sun, Guangshun Yi, Shuying Zhao, Depu Chen, Yuxiang Zhou, and Jing Cheng, Analytical Letters, vol. 34, 2001, pp. 1627-1637.
Article—*Stimuli-Responsive Poly(N-isopropylacrylamide) Photo- and Chemical-Induced Phase Transitions*, Advances in Polymer Science, pp. 50-65.
Article—*The Adsorptive Characteristics of Proteins for Polystyrene and Their Significance in Solid-Phase Immunoassays*, L. A. Cantaero, J. E. Butler, and J. W. Osborne, Analytical Biochemistry, vol. 105, 1980, pp. 375-382.
Article—*The Use of Self-Assembled Monolayers and a Selective Etch To Generate Patterned Gold Features*, Amit Kumar, Hans A. Biebuyck, Nicholas L. Abbott, and George M. Whitesides, Journal of the American Chemical Society, vol. 114, 1992, 2 pages.
Article—*Volume Phase Transition of N-Alkylacrylamide Gels*, S. Saito, M. Konno, and H. Inomata, Advances in Polymer Science, vol. 109, 1992, pp. 207-232.
Article—*Whole Blood Capcellia CD4/CD8 Immunoassay for Enumeration of CD4+ and CD8+ Peripheral T Lymphocytes*, Dominique Carrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.
8 Photographs of Accu-chek® Blood Glucose Meter.
*AMI Screen Printers*—Product Information, 4 pages.
*CELQUAT® SC-230M* (28-6830).
CELQUAT® SC-240C and SC-230M, from National Starch & Chemical, 1 page.
Polyquaternium-10, from National Starch & Chemical, 1 page.
*Dualita® Polymeric Microspheres*, from Pierce & Stevens Corp. a subsidiary of Sovereign Specialty Chemicals, Inc., 2 pages.
*Dynabeads® Biomagnetic Separation Technology—The Principle* from Dynal Biotech, 2 pages.
*ECCOSPHERES® glass microspheres—hollow glass microspheres* from Emerson & Cuming Composite Materials, Inc., 1 page.
*Fluorescent Microsphere Standards for Flow Cytometry and Fluorescence Microscopy* from Molecular Probes, pp. 1-8.
*FluoSpheres® Fluorescent Microspheres*, Product Information from Molecular Probes, Mar. 13, 2001, pp. 1-6.
*Magnetic Microparticles*, Polysciences, Inc. Technical Data Sheet 438, 2 pages.
*Making sun exposure safer for everyone* from Rohm and Haas Company (Bristol Complex), 2 pages.
Pamphlet—The ClearPlane® Easy Fertility Monitor.
*POSS Polymer Systems* from Hybrid Plastics, 3 pages.
*The colloidal state*, Introduction to Colloid and Surface Chemistry, $4^{th}$ Ed., 17 pages.
*Working With FluoSpheres® Fluorescent Microspheres*, Properties and Modifications, Product Information from Molecular Probes, Mar. 9. 2001, pp. 1-5.
PCT Search Report for PCT/US03/21520, Dec. 15, 2003.
PCT Search Report for PCT/US02/37653, Apr. 7, 2004.
PCT Search Report for PCT/US03/28628, Mar. 18, 2004.
PCT Search Report for PCT/US03/34543, Apr. 6, 2004.
PCT Search Report for PCT/US03/34544, Apr. 20, 2004.
PCT Search Report and Written Opinion for PCT/US2004/013180, Aug. 17, 2004.
Wei, et al., U.S. Appl. No. 10/325,429, filed Dec. 19, 2002, Self-Calibrated Flow-Through Assay Devices.
Yang, et al., U.S. Appl. No. 10/406,577, filed Apr. 3, 2003, Assay Devices That Utilize Hollow Particles.
Wei, et al., U.S. Appl. No. 10/325,614, filed Dec. 19, 2002, Reduction Of The Hook Effect In Membrane-Based Assay Devices.
Wei, et al., U.S. Appl. No. 10/406,631, filed Apr. 3, 2003, Reduction Of The Hook Effect In Assay Devices.
Wei, et al., U.S. Appl. No. 10/718,997, filed Nov. 21, 2003, Extension Of The Dynamic Detection Range Of Assay Devices.
Xuedong Song, U.S. Appl. No. 10/719,976, filed Nov. 21, 2003, Method For Extending The Dynamic Detection Range Of Assay Devices.
Yang, et al., U.S. Appl. No. 10/741,434, filed Dec. 19, 2003, Laminated Assay Devices.
Yang, et al., U.S. Appl. No. 10/742,589, filed Dec. 19, 2003, Flow Control Of Electrochemical-Based Assay Devices.
Yang, et al., U.S. App. No. 10/742,590, filed Dec. 19, 2003, Flow-Through Assay Devices.
Xuedong Song, U.S. Appl. No. 10/718,989, filed Nov. 21, 2003, Membrane-Based Lateral Flow Assay Devices That Utilize Phosphorescent Detection.
David S. Cohen, U.S. Appl. No. 10/836,093, filed Apr. 30, 2004, Optical Detection Systems.
Boga, et al., U.S. Appl. No. 10/790,617, filed Mar. 1, 2004, Assay Devices Utilizing Chemichronic Dyes.

Article—*New Use of Cyanosilane Coupling Agent for Direct Binding of Antibodies to Silica Supports. Physicochemical Characterization of Molecularly bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.

PCT Search Report and Written Opinion for PCT/US2004/006412, Sep. 28, 2004.

PCT Search Report and Written Opinion for PCT/US2004/006414, Sep. 28, 2004.

PCT Search Report and Written Opinion for PCT/US2004/032938, Jan. 21, 2005.

Article—*Application of rod-like polymers with ionophores as Langmuir-Blodgett membranes for Si-Based ion sensors*, Sensors & Actuators B, vol. 6, 1992, pp. 211-216.

Article—*Photolithography of self-assmbled monolayers: optimization of protecting groups by an electroanalytical method*, Can.J. Chem. vol. 74, 1996, pp. 2509-2517.

\* cited by examiner

METHOD OF REDUCING THE SENSITIVITY OF ASSAY DEVICES

BACKGROUND OF THE INVENTION

Various analytical procedures and devices are commonly employed in flow-through assays to determine the presence and/or concentration of analytes that within a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample. Unfortunately, many conventional immunoassay assays encounter problems when used to measure test samples that possess a high analyte concentration. For instance, elevated levels of C-reactive protein ("CRP") are sometimes indicative of certain diseases, such as heart disease. However, even normal blood samples may contain a high CRP concentration, often within the "milligrams per milliliter" range. Because most conventional immunoassays are designed to detect analyte concentrations in the "nanograms per milliliter" range, they will almost undoubtedly give positive results of the presence of CRP for all test samples, including those having a normal CRP concentration. This may be particularly troubling to consumers who are themselves performing the assay with a disposable device.

As such, a need currently exists for an assay device that is capable of detecting the presence of an analyte in circumstances where a "normal" test sample still contains relatively high levels of the analyte.

SUMMARY OF THE INVENTION

In accordance with one embodiment of the present invention, a method for detecting an analyte residing in a test sample is disclosed. The method comprises:

i) providing a flow-through assay device comprising a porous membrane that is in fluid communication with detection probes conjugated with a specific binding member for the analyte, wherein the assay device defines a scavenging zone and a detection zone, each of the zones containing a capture regent for the analyte;

ii) contacting the scavenging zone with the test sample so that a quantity of the analyte less than or equal to a predefined base quantity binds to the capture reagent at the scavenging zone;

iii) contacting the conjugated detection probes with the test sample; and iv) allowing the test sample and the conjugated detection probes to flow to the detection zone so that the conjugated detection probes or complexes thereof bind to the capture reagent and generate a detection signal, wherein the quantity of analyte in the test sample in excess of the predefined base quantity is proportional to the intensity of the detection signal.

In accordance with another embodiment of the present invention, a method for detecting an antigen residing in a test sample is disclosed. The method comprises:

i) providing a flow-through assay device comprising a porous membrane that is in fluid communication with detection probes conjugated with a specific binding member for the antigen, wherein the assay device defines a scavenging zone and a detection zone located downstream from the scavenging zone, each of the zones containing a capture reagent capable of specifically binding to the antigen, wherein the capture reagent of the scavenging zone includes an antibody;

ii) contacting the scavenging zone with the test sample so that a quantity of the antigen less than or equal to a predefined base quantity binds to the antibody at the scavenging zone;

iii) thereafter, contacting the conjugated detection probes with the test sample; and iv) allowing the test sample and the conjugated detection probes to bind to the capture reagent at the detection zone and generate a detection signal, wherein the quantity of antigen in the test sample in excess of the predefined base quantity is proportional to the intensity of the detection signal.

In accordance with still another embodiment of the present invention, a flow-through assay device is disclosed for detecting an analyte residing in a test sample. The assay device comprises a porous membrane that is in fluid communication with detection probes conjugated with a specific binding member for the analyte. The assay device defines a scavenging zone that contains a capture reagent configured to bind to a quantity of the analyte less than or equal to a predefined base quantity. The assay device further defines a detection zone within which a capture reagent is immobilized that is configured to bind to the conjugated detection probes or complexes of the conjugated detection probes and any analyte that does not bind to the scavenging zone. The detection zone is configured to generate a detection signal so that the quantity of analyte in the test sample in excess of the predefined base quantity is proportional to the intensity of the detection signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
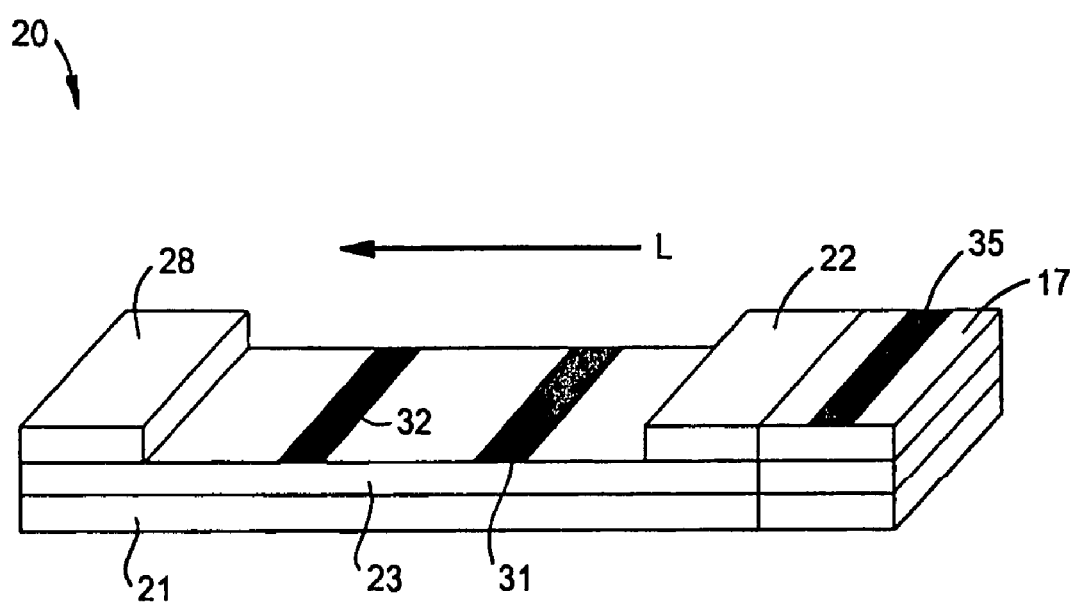
FIG. 1 is a perspective view of one embodiment of a flow-through assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a material suspected of containing the analyte. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. The test sample may be pretreated prior to use, such as preparing plasma from blood, diluting viscous fluids, and the like. Methods of treatment may involve filtration, precipitation, dilution, distillation, mixing, concentration, inactivation of interfering components, and the addition of reagents. Besides physiological fluids, other liquid samples may be used such as water, food products and the like for the performance of environmental or food production assays. In addition, a solid material suspected of containing the analyte may be used as the test sample. In some instances it may be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a flow-through assay device for detecting an analyte residing in a test sample. The device utilizes a scavenging zone that contains a capture reagent for the analyte of interest. The capture reagent may capture a quantity of the analyte that is less than or equal to a predefined base quantity of the analyte, such as a quantity considered "normal" for a particular test sample. Thus, the capture reagent is able to prevent some of the analyte from being detected. In this manner, the sensitivity of the assay device may be reduced in a simple, inexpensive, yet effective manner.

Referring to FIG. 1, for instance, one embodiment of a flow-through assay device 20 that may be formed according to the present invention will now be described in more detail. As shown, the device 20 contains a porous membrane 23 optionally supported by a rigid material 21. In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 may assist in promoting capillary action and fluid flow through the membrane 23.

To initiate the detection of an analyte within the test sample, a user may apply the test sample to a portion of the porous membrane 23 (either directly or indirectly) through which it may then travel in the direction illustrated by arrow "L" in FIG. 1. For example, as shown, the test sample is applied to a sampling pad 17 that is in fluid communication with the porous membrane 23. Some suitable materials that may be used to form the sampling pad 17 include, but are not limited to, nitrocellulose, cellulose, porous polyethylene pads, and glass fiber filter paper.

The sampling pad 17 contains a scavenging zone 35. Alternatively, the scavenging zone 35 may be formed directly on the porous membrane 23, or at any other location of the assay device 20. Regardless of its location, the scavenging zone 35 includes one or more capture reagents having a specific binding member for the analyte of interest. A specific binding member generally refers to a member of a specific binding pair, i.e., two different molecules where one of the molecules chemically and/or physically binds to the second molecule.

For example, in some embodiments, the capture reagent may include antigens, haptens, protein A or G, neutravidin, avidin, streptavidin, captavidin, antibodies (e.g., polyclonal, monoclonal, etc.), and complexes thereof. When utilized, the antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The capture reagent of the scavenging zone 35 serves as a binding site for the analyte. Specifically, analytes, such as antigens, typically have two or more binding sites (e.g., epitopes). One of these binding sites binds to the capture reagent at the scavenging zone 35. Desirably, the capture reagent is immobilized (diffusively or non-diffusively) within the scavenging zone 35 to prohibit the analyte from later being captured at the detection zone 31 (discussed below). Alternatively, however, the capture reagent may simply be formed from a compound that will not be captured at the detection zone 31. For example, the capture reagent may be identical to an additional capture reagent used at the detection zone 31. In this manner, the capture reagent at the scavenging zone 35 will occupy the only epitope of the analyte that would be able to bind to the capture reagent at the detection zone 31.

The scavenging zone 35 may generally provide any number of distinct regions (e.g., lines, dots, etc.). Each region may contain the same capture reagent, or may contain different capture reagents for capturing multiple analytes. The regions may be disposed in the form of lines in a direction that is substantially perpendicular to the flow of the test sample through the assay device 20. Likewise, in some embodiments, the regions may be disposed in the form of lines in a direction that is substantially parallel to the flow of the test sample through the assay device 20. Regardless of the particular configuration of the scavenging zone 35 selected, the quantity of the capture reagent at the scavenging zone 35 is predetermined and tailored to capture a quantity of the analyte that is less than or equal to a predefined base quantity, such as a quantity considered "normal" for the particular application. For instance, a blood sample containing less than about 10 micrograms of C-reactive protein ("CRP") per milliliter may be considered "normal" under some circumstances. In this case, the quantity of CRP-specific antibodies utilized at the scavenging zone 35 may be sufficient to bind to a maximum of 10 micrograms per milliliter of CRP. Any additional CRP will pass through the scavenger zone 35 and be detected at the detection zone 31 (discussed below).

Referring again to FIG. 1, the test sample (including any free analyte) travels from the sampling pad 17 to a conjugate pad 22 that is in fluid communication with at least one end of the sampling pad 17. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used in the present invention.

To facilitate accurate detection of the presence or absence of any remaining analyte within the test sample, a predetermined amount of detection probes are applied at various locations of the device 20. Any substance generally capable of generating a signal that is detectable visually or by an instrumental device may be used as detection probes. Various suitable substances may include chromogens; catalysts; luminescent compounds (e.g., fluorescent, phosphorescent, etc.); radioactive compounds; direct visual labels, including colloidal metallic (e.g., gold) and non-metallic particles, dye particles, enzymes or substrates, or organic polymer latex particles; liposomes or other vesicles containing signal producing substances; and so forth. For instance, some enzymes suitable for use as detection probes are disclosed in U.S. Pat. No. 4,275,149 to Litman, et al., which is incorporated herein in its entirety by reference thereto for all purposes. Some examples of suitable fluorescent molecules, for instance, include, but are not limited to, fluorescein, europium chelates, phycobiliprotein, rhodamine and their derivatives and analogs. Other suitable detection probes may be described in U.S. Pat. No. 5,670,381 to Jou, et al. and U.S. Pat. No. 5,252,459 to Tarcha, et al., which are incorporated herein in their entirety by reference thereto for all purposes.

The detection probes, such as described above, may be used alone or in conjunction with a particle (sometimes referred to as "beads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), and so forth, may be used. Further, synthetic particles may also be utilized. For example, in one embodiment, latex particles that are labeled with a fluorescent or colored dye are utilized. Although any latex particle may be used in the present invention, the latex particles are typically formed from polystyrene, butadiene styrenes, styreneacrylic-vinyl terpolymer, polymethylmethacrylate, polyethyl methacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex particles include carboxylated latex beads sold by Bang's Laboratory, Inc.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

Figure 2:
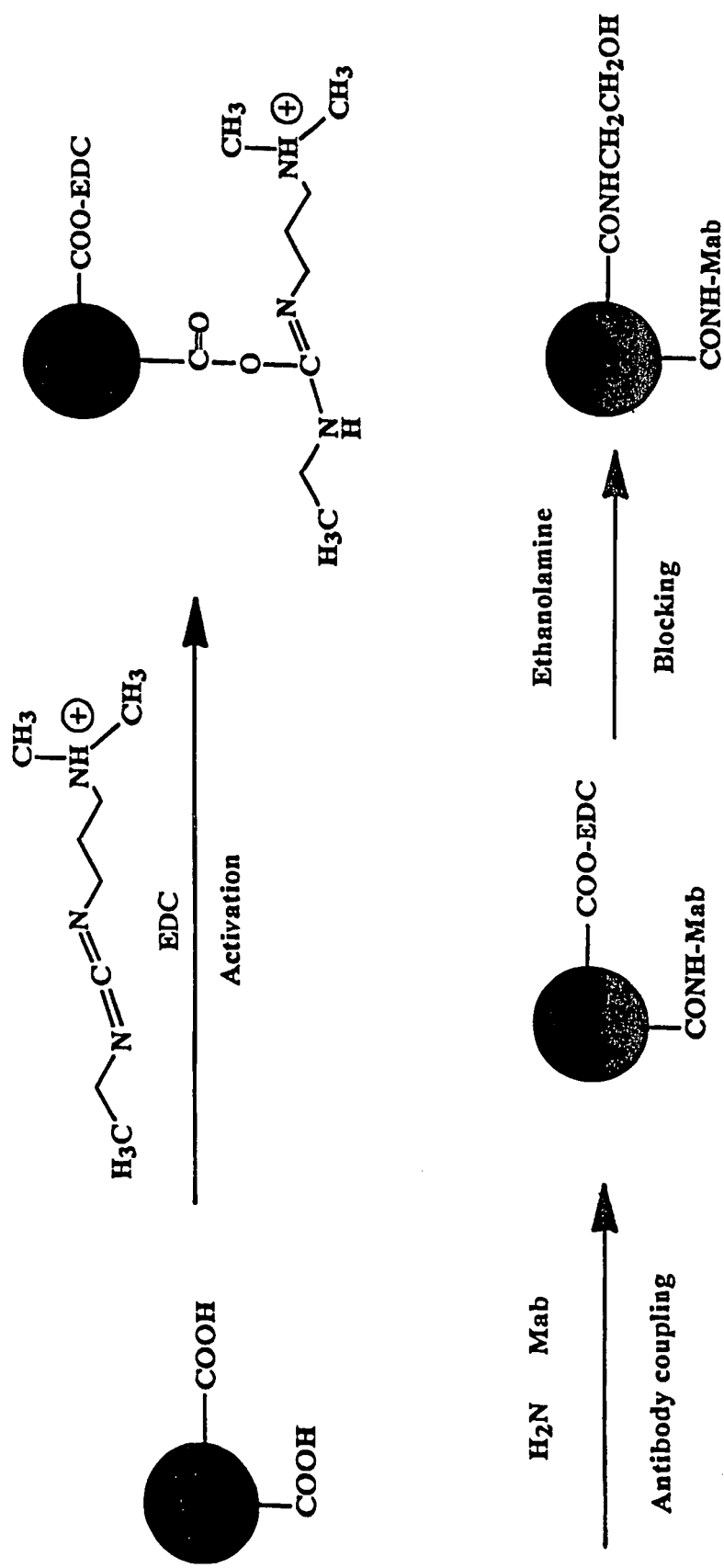
FIG. 2 is a graphical illustration of one embodiment for covalently conjugating an antibody to a detection probe.

In some instances, the detection probes are modified in some manner so that they are more readily able to bind to the analyte. In such instances, the detection probes may be modified with specific binding members that are adhered thereto to form conjugated probes. These specific binding members may be the same or different than the specific binding members described above. Specific binding members may generally be attached to detection probes using any of a variety of well-known techniques. For instance, covalent attachment of specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, in certain cases, such as poly(thiophenol), the particles are capable of direct covalent linking with a protein without the need for further modification. For example, referring to FIG. 2, one embodiment of the present invention for covalently conjugating a particle-containing detection probe is illustrated. As shown, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). As shown, the resulting detection probes may then be blocked with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

Referring again to FIG. 1, the assay device 20 also contains a detection zone 31 within which is immobilized a capture reagent that is capable of binding to the conjugated detection probes. For example, in some embodiments, the capture reagent may be a biological capture reagent. Such biological capture reagents are well known in the art and may include, but are not limited to, antigens, haptens, protein A or G, neutravidin, avidin, streptavidin, captavidin, primary or secondary antibodies (e.g., polyclonal, monoclonal, etc.), and complexes thereof. The capture reagent serves as a stationary binding site for complexes formed between the analyte and conjugated detection probes. Upon reaching the detection zone 31, one of the binding sites of the analyte is occupied by the specific binding member of the conjugated probe. However, the free binding site of the analyte may bind to the immobilized capture reagent. Upon being bound to the immobilized capture reagent, the complexed probes form a new ternary sandwich complex.

The detection zone 31 may generally provide any number of distinct detection regions so that a user may better determine the concentration of a particular analyte within a test sample. Each region may contain the same capture reagents, or may contain different capture reagents for capturing multiple analytes. For example, the detection zone 31 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions may be disposed in the form of lines in a direction that is substantially parallel to the flow of the test sample through the assay device.

Although the detection zone 31 may indicate the presence of an analyte, it is often difficult to accurately determine the relative concentration of the analyte within the test sample under actual test conditions. Thus, the assay device 20 may also include a calibration zone 32. In this embodiment, the calibration zone 32 is formed on the porous membrane 23 and is positioned downstream from the detection zone 31. The calibration zone 32 is provided with a capture reagent that is capable of binding to probes, whether uncaptured detection probes or separate calibration probes, which pass through the detection zone 31. Similar to the detection zone 31, the calibration zone 32 may also provide any number of distinct calibration regions in any direction so that a user may better determine the concentration of a particular analyte within a test sample.

Each region may contain the same capture reagents, or may contain different capture reagents for capturing different types of probes. The capture reagents utilized in the calibration zone 32 may be the same or different than the capture reagents used in the detection zone 31. In one embodiment, the capture reagent for the calibration zone 32 is a polyelectrolyte, such as described in U.S. Publication No. 2003/0124739 to Sono, et al., which is incorporated herein its entirety by reference thereto for all purposes. When utilized, the polyelectrolyte may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethyleneimine; epichlorohydrin-functionalized polyamines and/or polyamidoamines, such as poly (dimethylamine-co-epichlorohydrin); polydiallyldimethylammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridnium iodide) and poly(styryl-b-acrylic acid), both of which are available from Polymer Source, Inc. of Dorval, Canada.

Although any polyelectrolyte may generally be used, the polyelectrolyte selected for a particular application may vary depending on the nature of the detection probes, the porous membrane, and so forth. In particular, the distributed charge of a polyelectrolyte allows it to bind to substances having an opposite charge. Thus, for example, polyelectrolytes having a net positive charge are often better equipped to bind with probes that are negatively charged, while polyelectrolytes that have a net negative charge are often better equipped to bind to probes that are positively charged. Thus, in such instances, the ionic interaction between these molecules allows the required binding to occur within the calibration zone 32. Nevertheless, although ionic interaction is primarily utilized to achieve the desired binding in the calibration zone 32, it has also been discovered that polyelectrolytes may bind with detection probes having a similar charge.

The calibration regions may be pre-loaded on the porous membrane 23 with different amounts of the capture reagent so that a different signal intensity is generated by each calibration region upon migration of the probes. The overall amount of capture reagent within each calibration region may be varied by utilizing calibration regions of different sizes and/or by varying the concentration or volume of the capture reagent in each calibration region. If desired, an excess of detection probes may be employed in the assay device 20 so that each calibration region reaches its full and predetermined potential for signal intensity. That is, the amount of uncaptured detection probes that are deposited upon calibration regions are predetermined because the amount of the capture reagent employed on the calibration regions is set at a predetermined and known level. In the alternative, a predetermined amount of separate calibration probes may be used that are configured to only bind to the capture reagent at the calibration zone 32.

Figure 3:
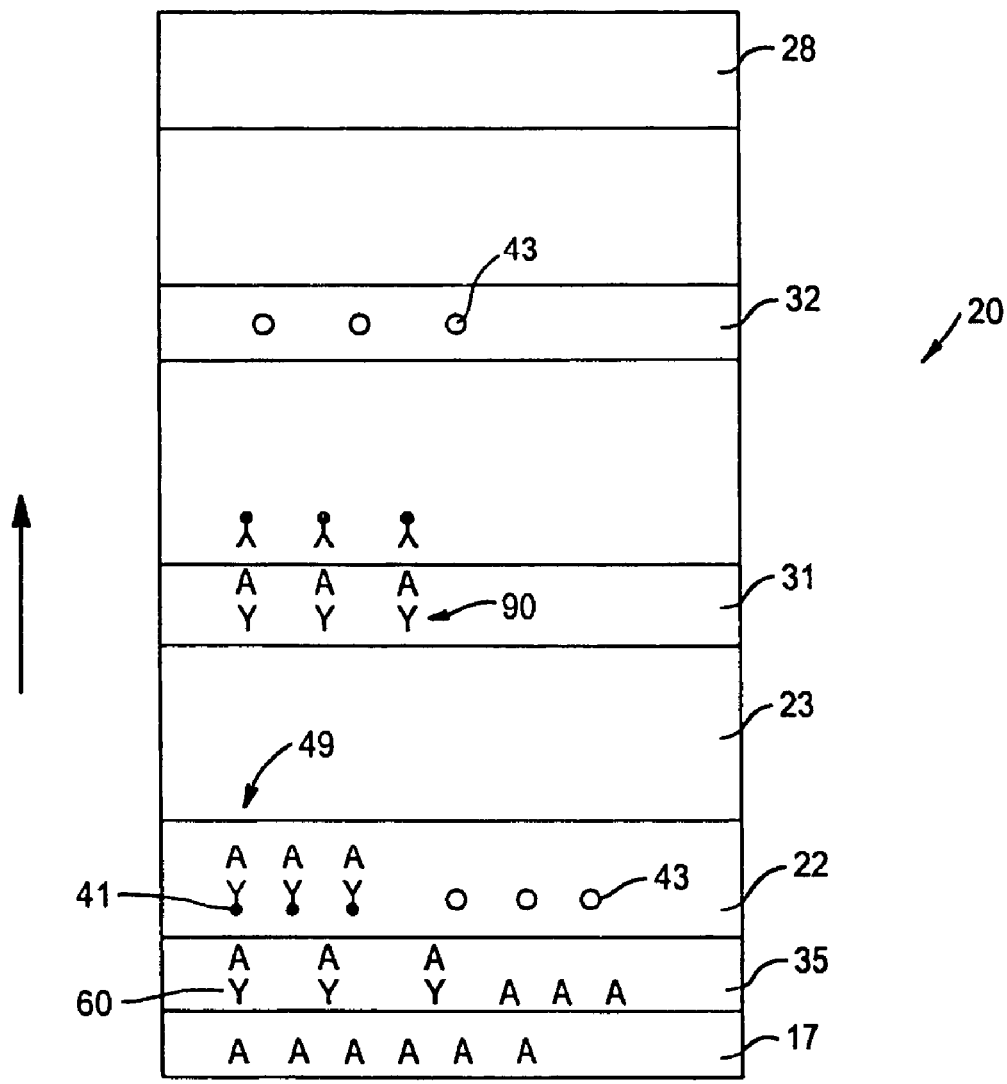
FIG. 3 is a graphical illustration of the mechanism used for one embodiment of a sandwich assay format of the present invention.

Referring to FIG. 3, one embodiment of a method for detecting the presence of an analyte will now be described in more detail. Initially, a test sample containing an analyte A is applied to the sampling pad 17. At the sampling pad 17, a certain quantity of the analyte A binds to a capture reagent 60 immobilized at the scavenging zone 35, such as an amount less than or equal to a predefined base quantity of analyte considered "normal" for the particular test sample. From the sampling pad 17, any analyte A in excess of the predefined base quantity travels in the direction "L" to the conjugate pad 22, where it mixes with conjugated detection probes 41 and calibration probes 43 (may or may not be conjugated). In this embodiment, the excess analyte A binds with the conjugated detection probes 41 to form analyte/conjugated probe complexes 49. Because the scavenging zone 35 is positioned upstream from the conjugate pad 22, it is not necessary to supply detection probes 41 for binding to any of the analyte A that is already captured by the scavenging zone 35. In this manner, the overall amount of required probes is reduced, which provides substantial cost savings.

At the detection zone 31, the complexes 49 are captured by a capture reagent 90. If desired, the capture reagent 60 at the scavenging zone 35 is identical to the capture reagent 90. Thus, should any of the capture reagent 60 somehow become free from the scavenging zone 35 and travel to the detection zone 31, it will not bind to the capture reagent 90 and adversely impact the desired reduction in detection sensitivity. Further, the calibration probes 43 travel through the detection zone 31 to bind with a capture reagent (not shown) at the calibration zone 32.

Once captured, the signal of the probes at the detection zone 31 and calibration zone 32 may be measured using any known method of detection, such as visually or with a reading device. Regardless of the technique utilized, the quantity of the analyte in excess of the predefined base quantity may be ascertained by correlating the emitted signal, $I_s$, of the probes captured at the detection zone 31 to a predetermined analyte concentration. In some embodiments, the intensity signal, $I_s$, may also be compared with the emitted signal, $I_c$, of probes captured at the calibration zone 32. The total amount of the probes at the calibration zone 32 is predetermined and known and thus may be used for calibration purposes. For example, in some embodiments (e.g., sandwich assays), the quantity of analyte in excess of the predefined base quantity is directly proportional to the ratio of $I_s$ to $I_c$. In other embodiments (e.g., competitive assays), the quantity of analyte in excess of the predefined base quantity is inversely proportional to the ratio of $I_s$ to $I_c$. Based upon the intensity range in which the detection zone 31 falls, the general concentration range for the analyte may be determined. As a result, calibration and sample testing may be conducted under approximately the same conditions at the same time, thus providing reliable quantitative or semi-quantitative results, with increased sensitivity.

If desired, the ratio of $I_s$ to $I_c$ may be plotted versus the analyte concentration for a range of known analyte concentrations to generate a calibration curve. To determine the quantity of analyte in an unknown test sample that is in excess of a predefined base quantity, the signal ratio may then be converted to analyte concentration according to the calibration curve. It should be noted that alternative mathematical relationships between $I_s$ and $I_c$ may be plotted versus the analyte concentration to generate the calibration curve. For example, in one embodiment, the value of $I_s/(I_s+I_c)$ may be plotted versus analyte concentration to generate the calibration curve.

Although various embodiments of device configurations have been described above, it should be understood, that a device of the present invention may generally have any configuration desired, and need not contain all of the components described above. Various other device configurations, for instance, are described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

Various assay formats may also be used to test for the presence or absence of an analyte using the assay device of the present invention. For instance, in the embodiment described above, a "sandwich" format is utilized. Other examples of such sandwich-type assays are described in. by U.S. Pat. No. 4,168,146 to Grubb, et al. and U.S. Pat. No. 4,366,241 to Tom, et al., which are incorporated herein in their entirety by reference thereto. An alternative technique is the "competitive-type" assay. In a "competitive-type" assay, the detection probe is typically a labeled analyte or analyte-analog that competes for binding of an antibody with any unlabeled analyte present in the sample. Competitive assays are sometimes used for detection of hapten analytes, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes.

The present inventor has discovered that a scavenging zone may be utilized to reduce the sensitivity of an assay device by capturing a quantity of an analyte within a test sample that is less than or equal to a predefined base quantity, such as a quantity that is considered "normal" for a particular test sample. In this manner, the analyte captured at the scavenging zone is not detected. Desirably, the test sample contacts the scavenging zone before mixing with detection probes minimize the required amount of detection probes and achieve substantial cost savings.

The present invention may be better understood with reference to the following examples.

Example 1

The ability to form a lateral flow assay device according to the present invention was demonstrated. A nitrocellulose porous membrane (HF 120 from Millipore, Inc.) having a length of approximately 30 centimeters was laminated onto supporting cards. Goldline™ (a polylysine solution obtained from British Biocell International) was stripped onto the membrane to form a calibration line. In addition, monoclonal antibody for C-reactive protein (Mab2) (A#5804, available from BiosPacific, concentration of 1 milligram per milliliter) was immobilized on the porous membrane to form a detection line. The membrane samples were then dried for 1 hour at a temperature of 37° C. A cellulosic fiber wicking pad (Millipore, Inc. Co.) was attached to one end of the membrane. 120 microliters of gold particles conjugated with C-reactive protein (Mab1) (A#5811, available from BiosPacific, Inc.) was mixed with 250 microliters of sucrose in 630 microliters of water. The suspension was then loaded onto a 20-centimeter long glass fiber conjugate pad (Millipore Co.). The glass fiber pad was then dried at 37° C. overnight and laminated to the supporting card. The nitrocellulose membrane was attached to one end of the conjugate pad, while a sample pad was attached to the other end.

Various types of sample pads were evaluated. Specifically, the sample pads tested were a nylon membrane available from Millipore, a nitrocellulose membrane available from Schleicher & Schuell, and a nitrocellulose membrane available from Millipore. A scavenging antibody, i.e., monoclonal antibody for C-reactive protein (Mab2) (A#5804, available from BiosPacific Inc.), was applied to the sampling pads at various concentrations to form a scavenging zone. Specifically, the scavenging antibody was applied to the nylon membrane at concentrations of 0 and 0.5 milligrams per milliliter, to the Schleicher & Schuell membranes at a concentration of 0.5 milligrams per milliliter, and to the Millipore membrane at a concentration of 2.36 milligrams per milliliter. Each membrane was then dried at 37° C., cut into 4-millimeter strips, and put onto the conjugate pad to complete the assembly of a 4-millimeter full strip.

80 microliters of a C-reactive protein solution (170 nanograms per milliliter) was applied to each sampling pad. Each assay was visually observed for the detection signal intensity. For the nylon membrane sample pad, the detection signal intensity was the same for scavenging antibody concentrations of 0 and 0.5 milligrams per milliliter. For the Schleicher & Schuell nitrocellulose membrane, the detection signal was detected, but its intensity was reduced. For the Millipore nitrocellulose sample pad, the detection line gave no signal.

Example 2

A lateral flow assay device was formed as described above in Example 1, except that the sample pad was made from a membrane containing ultra-high molecular weight polyethylene spherical particles, which was obtained from the Porex Corporation of Fairburn, Ga. under the name "Lateral-Flo" membrane. In addition, the concentration of the scavenging antibody was 1 milligram per milliliter. To this sample pad, a solution containing 40 microliters of 2% Tween 20 and 40 microliters of C-reactive protein was applied. The C-reactive protein concentrations tested were 0, 50 and 500 nanograms per milliliter. Comparative samples were also tested that did not contain the scavenging antibody. The assay was allowed to develop for approximately 10 minutes, and the detection line intensity was then read using a reflectance reader.

Figure 4:
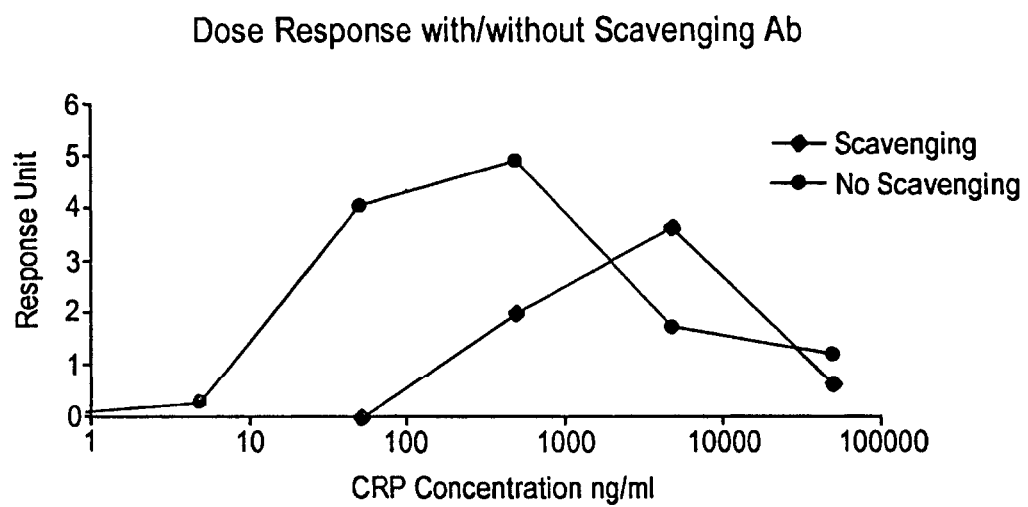
FIG. 4 shows the results of Example 2, in which the intensity of the detection line for an assay using a scavenging zone was compared to the intensity of the detection line for an assay without a scavenging zone.

For the samples containing the scavenging antibody, the detection line was negative for C-reactive protein concentrations of 0 and 50 nanograms per milliliter. For the comparative sample, a C-reactive protein concentration of 50 nanograms per milliliter resulted in a strong positive signal for the detection line. The results are shown in FIG. 4.

Example 3

A lateral flow assay device was formed as described above in Example 1, except that the scavenging antibody was monoclonal antibody for C-reactive protein (Mab1) (A#5811, available from BiosPacific) at a concentration of 5.7 milligrams per milliliter. To the sampling pad, 1 microliter of various C-reactive protein solutions (CRP concentrations of 1000, 10000 and 50000 nanograms per milliliter) were applied and run with 150 microliters of diluent (Tween:PBS 10:6). The assay was allowed to develop for approximately 10 minutes. The detection signal intensity was visually observed. The device gave a positive result for a C-reactive protein concentration of 50 nanograms per milliliter, but a negative for C-reactive protein concentrations of 1 and 10 nanograms per milliliter.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting an analyte in a test sample, the method comprising:
   i) providing an assay device that comprises:
      a sampling pad that defines a scavenging zone in which is non-diffusively immobilized a first capture reagent configured to specifically bind with the analyte;
      a conjugate pad that contains detection probes and optional calibration probes, the detection probes being conjugated with a first binding member configured to specifically bind with the analyte; and
      a porous membrane in fluid communication with the sampling pad and the conjugate pad, the porous membrane defining a detection zone in which is immobilized a second capture reagent configured to specifically bind with the analyte and a calibration zone within which is immobilized a third capture reagent including a polyelectrolyte having a net charge opposite to that of and configured to bind with the detection probes, the calibration probes, or combinations thereof,
   wherein the detection zone and the calibration zone are located downstream from the sampling pad and the conjugate pad;
   ii) contacting the assay device with the test sample, wherein a quantity of the analyte in the test sample less than or equal to a predefined base quantity binds to the first capture reagent at the scavenging zone and a quantity of the analyte in excess of the predefined base quantity binds to the specific binding member of the detection probes to form complexes that flow through the porous membrane and bind to the second capture reagent in the detection zone to generate a detection signal, and wherein the detection probes, the calibration probes, or a combination thereof, flow through the porous membrane and bind to the third capture reagent at the calibration zone to generate a calibration signal;

iii) detecting the intensity of the detection signal and the calibration signal; and iv) comparing the intensity of the detection signal to the intensity of the calibration signal, wherein the quantity of the analyte within the test sample in excess of the predefined base quantity is proportional to the intensity of the detection signal calibrated by the intensity of the calibration signal.

2. A method as defined in claim 1, wherein said first capture reagent at said scavenging zone is selected from the group consisting of antigens, haptens, protein A or G, neutravidin, avidin, streptavidin, captavidin, antibodies, and complexes thereof.

3. A method as defined in claim 1, wherein said second capture reagent at said detection zone is selected from the group consisting of antigens, haptens, protein A or G, neutravidin, avidin, streptavidin, captavidin, antibodies, and complexes thereof.

4. A method as defined in claim 1, wherein said capture reagents at said scavenging zone and said detection zone are substantially identical.

5. A method as defined in claim 1, wherein said detection probes comprise a substance selected from the group consisting of chromogens, catalysts, luminescent compounds, radioactive compounds, direct visual labels, liposomes, and combinations thereof.

6. A method as defined in claim 1, wherein the conjugate pad is located downstream from the sampling pad.

7. A method as defined in claim 1, wherein the analyte includes an antigen.

8. A method as defined in claim 7, wherein the specific binding member of the detection probes includes an antibody.

9. A method as defined in claim 8, wherein the first capture reagent and the second capture reagent include antibodies that bind to the same epitope of the analyte.

10. A method as defined in claim 7, wherein the antigen includes C-reactive protein.

11. A method as defined in claim 1, wherein the test sample is blood or derived from blood.

12. A method as defined in claim 11, wherein the analyte includes C-reactive protein.

13. A method as defined in claim 12, wherein the predefined base quantity is about 10 micrograms of C-reactive protein per milliliter of the test sample.

14. A method as defined in claim 1, wherein the assay device further comprises a wicking pad in fluid communication with the porous membrane and located downstream from the detection zone and the calibration zone.

15. A method as defined in claim 1, wherein said polyelectrolyte has a net positive charge.

16. A method as defined in claim 15, wherein said polyelectrolyte is selected from the group consisting of polylysine, polyethyleneimine, epichlorohydrin-functionalized polyamines or polyamidoamines, polydiallyldimethyl-ammonium chloride, cationic cellulose derivatives, and combinations thereof.

17. A method as defined in claim 1, wherein said polyelectrolyte has a net negative charge.

18. A method as defined in claim 1, wherein the detection probes comprise latex microparticles.

* * * * *